United States Patent
Shim et al.

(10) Patent No.: US 9,008,763 B2
(45) Date of Patent: Apr. 14, 2015

(54) ARRHYTHMIA DIAGNOSIS METHOD AND DEVICE

(75) Inventors: Eun Bo Shim, Gangwon-do (KR); Ki Moo Lim, Gangwon-do (KR)

(73) Assignee: CU Medical Systems, Inc., Gangwon (KR)

( * ) Notice: Subject to any disclaimer, the term of this patent is extended or adjusted under 35 U.S.C. 154(b) by 0 days.

(21) Appl. No.: 13/581,088

(22) PCT Filed: Feb. 25, 2011

(86) PCT No.: PCT/KR2011/001360
§ 371 (c)(1),
(2), (4) Date: Dec. 3, 2012

(87) PCT Pub. No.: WO2011/105859
PCT Pub. Date: Sep. 1, 2011

(65) Prior Publication Data
US 2013/0079653 A1    Mar. 28, 2013

(30) Foreign Application Priority Data
Feb. 26, 2010   (KR) .......................... 10-2010-0017665

(51) Int. Cl.
*A61B 5/04*     (2006.01)
*A61B 5/0456*   (2006.01)
*A61B 5/046*    (2006.01)
*A61B 5/0464*   (2006.01)

(52) U.S. Cl.
CPC ............... *A61B 5/0456* (2013.01); *A61B 5/046* (2013.01); *A61B 5/0464* (2013.01)

(58) Field of Classification Search
None
See application file for complete search history.

(56) References Cited

U.S. PATENT DOCUMENTS

| 2007/0027390 A1 | 2/2007 | Maschke et al. |
| 2009/0112106 A1* | 4/2009 | Zhang .......................... 600/509 |

FOREIGN PATENT DOCUMENTS

| JP | H0622915 A | 2/1994 |
| JP | H06149863 A | 5/1994 |
| WO | 0120552 A1 | 3/2001 |

OTHER PUBLICATIONS

Kim, et.al. Spatiotemporal Complexity of Ventricular Fibrillation Revealed by Tissue Mass Reduction in Isolated Swine Right Ventricle. J Clin Invest. Nov. 15, 1997:100(10):2486-500.*
Graux, P. et al., "Wavelength and Atrial Vulnerability: an Endocavitary Approach in Humans", PACE—Pacing and Clinical Electrophysiology, vol. 21, No. 1, Part II, Jan. 1998, pp. 202-208.

(Continued)

*Primary Examiner* — Brian T Gedeon
*Assistant Examiner* — Ankit Tejani
(74) *Attorney, Agent, or Firm* — Lowe Hauptman & Ham LLP (57) ABSTRACT

Disclosed is an arrhythmia-diagnosing method and device for diagnosing arrhythmias, such as fibrillation or tachycardia. The arrhythmia-diagnosing method includes the following steps: measuring (a) the heart characteristic length, and the (b) frequency and (c) conduction velocity of the cardiac electrical wave; and (d) determining the occurrence or absence of an arrhythmia by using the three parameters measured in steps (a) to (c). With this invention, it is possible to predict and diagnose an electrical wave tornado, one of the causes of arrhythmia, by using a non-dimensional parameter, to identify patients at risk of death or brain death due to an arrhythmia and to reduce the mortality of patients suffering from arrhythmias significantly.

9 Claims, 4 Drawing Sheets

(56) References Cited

OTHER PUBLICATIONS

Kojodjojo, P. et al., "Characterization of the Electroanatominal Substrate in Human Atrial Fibrillation: The Relationship between Changes in Atrial Volume, Refractoriness, Wavefront Propagation Velocities, and AF Burden", Journal of Cardiovascular Electrophysiology, vol. 18, No. 3, Mar. 1, 2007, pp. 269-275.

European Search Report dated Mar. 17, 2014 in related European Application No. 11747749.7, 11 pages.

Japanese Office Action dated Mar. 27, 2014 in related Japanese Application No. 2012-554940, 3 pages.

* cited by examiner

ARRHYTHMIA DIAGNOSIS METHOD AND DEVICE

SCOPE OF THE INVENTION

This invention relates to an arrhythmia-diagnosis method and device and, more specifically, to an arrhythmia-diagnosis method and device for assessing the risk of severe arrhythmias, such as fibrillation or tachycardia.

BACKGROUND OF THE INVENTION

Contraction of the heart induced by the electrical excitation of myocardial cells induces ejection of blood. During this electrical excitation, the calcium concentration in the myocardial cells changes, which activates the contractile machinery in the cells, thereby inducing coordinated mechanical contraction. The heart contains a group of cells that generates an electric rhythm, the pacemaker cells at the sinoatrial node, and an excitation medium, myocardial cells, both of which contribute to generating electrical wave propagation. In the pacemaker cells, electrical excitation is generated periodically at a frequency of 60 to 100 per minute. If this excitation is propagated to the myocardial cells normally, the heart undergoes repeated contraction and expansion, supplying blood to the body.

Figure 1:
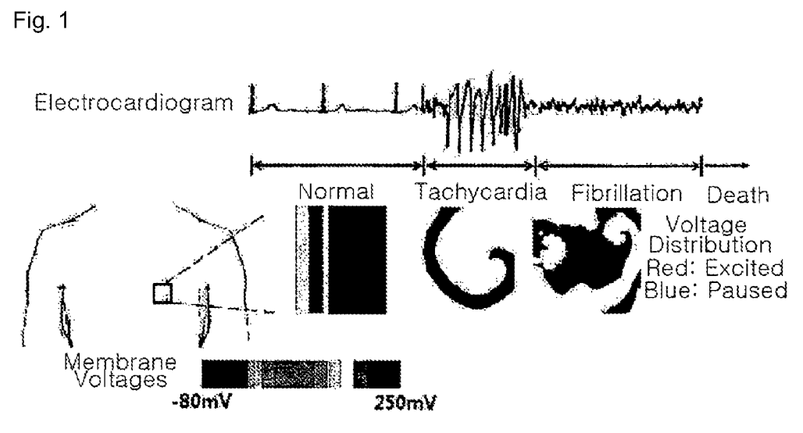
FIG. 1 explains tachycardia and fibrillation appearing in an arrhythmia patient.

As shown in FIG. 1, there are three kinds of arrhythmia: bradycardia, in which the electrical excitation rhythm is too slow; tachycardia, in which the electrical stimulation or conduction is too fast; and fibrillation, in which the heart rhythm is irregular and too fast. To date, no clear method has been proposed for diagnosing arrhythmias.

In most cases, doctors discover arrhythmias after their onset and then try to treat them. Currently, roughly 0.7% of the world's inhabitants suffer from arrhythmias, with 720,000 new arrhythmia patients seen annually. The cost of treating arrhythmias in the USA exceeds $18 billion and is growing. Ultimately, about 55% of cardiopaths die of arrhythmias. For the heart to eject blood normally, two conditions are necessary: first, the cardiac cells must contract synchronously, which requires that the electrical excitation of the cardiac cells occurs at essentially the same time; and second, the cardiac ventricles must relax for a sufficient period after contraction for the ventricles to fill. After contraction, very little blood remains in the ventricles. If the ventricles contract again in this state, only a small amount of blood will circulate, leading to peripheral tissue ischemia. To this end, a sufficiently long diastolic period is needed after the cardiac cells are excited electrically and contract.

There are many kinds of arrhythmia. Of these, arrhythmias attributable to an electrical wave tornado generated in the cardiac tissues are a major threat to life. In the event that an electrical wave tornado with a single center is generated and sustained in the heart, the cardiac cells are electrically excited continuously, with no relaxation. This results in rapid cardiac pulsation, which is called tachycardia. If there are several electrical wave tornados for any reason, the synchronism of the electrical excitation of the cardiac tissues is destroyed. This is fibrillation; if fibrillation is not stopped immediately, the patient may die. In brief, if fibrillation occurs, the cardiac pulsation becomes fast and the relaxation disappears, destroying the synchronized electrical excitation of the cardiac tissues. As a result, it is no longer possible for the heart to eject blood, which can lead to brain death or medical death.

Despite much research, no one has succeeded in identifying a diagnostic basis for the electrical wave tornado that is generated in the heart and the breakup of an electrical wave tornado into smaller ones. While diagnosis and examination items for diabetes, kidney disorders, coronary artery disorders, and cancers are available, there is none for diagnosing and predicting arrhythmias. In reality, a person who appears very healthy can suffer from a severe arrhythmia. That person often has an apparently normal pulse, even if the heart is heavily stressed. This means that arrhythmias such as tachycardia and fibrillation are irregular and difficult to predict.

SUMMARY OF THE INVENTION

In view of the above problems, the goal of our invention is to provide an arrhythmia-diagnosing device that is capable of predicting and diagnosing electrical wave tornados, one cause of arrhythmia, by using a non-dimensional parameter, to identify patients at risk of death or brain death from arrhythmias and significantly reduce the mortality of these patients.

One aspect of this invention is the arrhythmia-diagnosing method. This involves the following steps: measuring the (a) heart characteristic length; (b) frequency and (c) conduction velocity of the cardiac electrical wave; and (d) determining the occurrence or absence of arrhythmia using the three parameters measured in steps (a) to (c).

Another aspect of this invention is the arrhythmia-diagnosing device, which consists of: a measuring unit for measuring heart characteristic length; a second measuring unit for measuring the frequency of the cardiac electrical wave; a third measuring unit for measuring the conduction velocity of the cardiac electrical wave; and a determination unit for determining the occurrence or absence of arrhythmia using the three parameters obtained by the three measuring units.

Furthermore, the arrhythmia-diagnosing device includes an interface unit for sending data to an external device and a determination unit for determining the occurrence or absence of arrhythmia based on the heart characteristic length and the frequency and conduction velocity of the cardiac electrical wave input via the interface unit.

In addition, the arrhythmia-diagnosing device includes a first measuring unit for measuring the heart characteristic length, a second measuring unit for measuring the heart and outputting an electrocardiogram (ECG) signal, and a determination unit for calculating the frequency and conduction velocity of the cardiac electrical wave using the ECG signal, or using the ECG signal and heart characteristic length and determining the occurrence or absence of arrhythmia based on the heart characteristic length and the frequency and conduction velocity of the cardiac electrical wave.

With this invention, it is possible to predict and diagnose electrical wave tornados, one cause of arrhythmia, by using a non-dimensional parameter, to identify patients at risk of death or brain death due to arrhythmias, and to reduce their mortality significantly.

DETAILED DESCRIPTION OF THE DESIRED VERSIONS

Several versions of the arrhythmia-diagnosing method and the device used in our invention will now be described in detail.

Derivation of the Non-Dimensional Number

A dominant equation describing the conduction of the action voltage (corresponding to electrical excitation) in cardiac tissues is represented by the following formula, which incorporates the electrical activities of cardiac cells and describes the electrical wave phenomenon in terms of tissues $$\frac{\partial V}{\partial t} = -\frac{I_{ion} + I_{stim}}{C_m} + D\nabla^2 V \qquad \text{[Formula 1]}$$

Here, V is the inter-membrane voltage (mV) of myocardial cells, $I_{ion}$ is the current per unit area (pA/cm$^2$), which is the sum of the inter-membrane currents of the myocardial cells, the $I_{stim}$ is a stimulating current applied externally, $C_m$ is the capacitance per unit area (pF/cm$^2$), which is a capacitor component of a cell membrane, D is the conductivity coefficient, which equals $1/\rho SC_m$, i.e., an electric conductivity diffusion coefficient, where $\rho$ is the resistivity ($\Omega$·cm) of a cell and S is the surface area-to-volume ratio (cm$^{-1}$) of the cell, and $\nabla$ is a symbol indicating a spatial derivative. The left-side of Formula 1 is the time-dependent change in the voltage at a specific position in the ventricular tissue. The first term on the right side of Formula 1 is a source term representing the electrical excitation generated in the cardiac cells making up tissue. The second term on the right side of Formula 1 is an electrical wave diffusion term. Formula 1 is a typical partial differential reaction-diffusion-type equation. Using specified boundary conditions and initial conditions with a dominant equation like Formula 1, it is possible to quantify the action voltage propagation phenomenon in the heart. In Formula 1, the principal dimension of the respective terms is V/t (velocity/time).

To analyze the electrical wave conduction occurring in cardiac tissues, Formula 1 is converted into the non-dimensional equation shown in Formula 2. It is necessary to make an equation dimensionless to reduce a physical phenomenon that relies on many parameters to a question involving a small number of composite parameters, simplifying the physical phenomenon in a physical system. In other words, if the partial differential equation Formula 1 is made dimensionless, the non-dimensional numbers appearing as coefficients of the respective terms become representative parameters defining the physical phenomenon described by the equation. Even for an equation describing cardiac electrical wave conduction, it is possible to obtain a non-dimensional number by making the equation dimensionless. The non-dimensional number becomes an important criterion for determining the generation and change of the physical phenomenon: cardiac electrical wave conduction.

If the typical process for making an equation dimensionless is applied to Formula 1, we obtain the following dimensionless equation and see the one non-dimensional number [Sh].

$$\frac{\partial V^*}{\partial t^*} = -(I_{ion}^* + I_{stim}^*) + \frac{1}{[Sh]}\nabla^2 V^* \qquad \text{[Formula 2]}$$

In Formula 2, $V^*=V/\breve{V}$, $\nabla^*=L\nabla$, $t^*=t/T$, and $I^*=I/\breve{I}$ are all non-dimensional parameters. In this regard, $\breve{V}$ is the characteristic voltage, L is the characteristic length of the heart (the square root of the heart surface area or the cube root of heart volume), T denotes a characteristic time which is represented by L/v, and v is the conduction velocity (cm/s) of the action voltage. Accordingly, T is the time required for an electrical pulse to reach tissues of size L. $\breve{I}$ is the characteristic current, which is represented by $\breve{V}|\rho lC_m(A_s/A)$, where l is the length of a unit myocardial cell, $A_s$ is the surface area of the myocardial cell, and A is the cross-sectional area of the myocardial cell.

In Formula 2, the parameters of the dimensionless dominant equation include the shim number [Sh], represented by the following formula.

$$[Sh] = \rho SC_m vL = \frac{vL}{D} = \frac{f \cdot L^2}{D} = \frac{f \cdot L}{CV} \qquad \text{[Formula 3]}$$

In Formula 3, f is the frequency of the cardiac electrical wave, L is the characteristic length of the heart, and CV is the conduction or D/L.

The physical meaning of the shim number [Sh] is as follows: [Sh]=f·L/CV, i.e., the inertia of an electrical wave tending to be propagated in a given direction divided by the conduction tendency of an electrical wave (the tendency of an electrical wave to be dispersed uniformly with no directivity).

As [Sh] increases, the inertia of the electrical wave increases, which increases the probability of generating an electrical wave tornado. As [Sh] decreases, the electrical wave tends to be dispersed uniformly to the base. This reduces the directivity of the electrical wave and consequently increases the stability of the electrical wave.

Use of the Non-Dimensional Number in Diagnosing Arrhythmias

Formula 1 is the dominant equation of the cardiac electrical wave. In non-dimensional Formula 2, the non-dimensional number [Sh] is derived by making Formula 1 dimensionless. Consequently, the cardiac electrical wave is essentially decided by Sh, i.e., the pathological cardiac phenomenon depends on the non-dimensional number. In other words, [Sh] can be used for predicting and diagnosing the risk of tachycardia and fibrillation, which are severe arrhythmias. Even if the heart is normal and does not suffer from arrhythmia, [Sh] may be used as a basis for predicting and determining whether the electrical wave is generated normally in the cardiac tissues. Specifically, [Sh] changes during early myocardial hypertrophy resulting from different causes, such as aging and obesity. It might be possible to infer the reverse, i.e., myocardial hypertrophy, from Sh. In addition, [Sh] can be used to quantify the treatment effects in arrhythmia patients by comparing [Sh] before and after treatment.

Clinically, arrhythmias can be diagnosed by measuring [Sh] in a patient and predicting the propagation tendency of cardiac electricity. Any cardiac pathology would affect Sh. For example, if the myocardial hypertrophy accompanying heart disease is pathological, a large number of fibroblasts, which have very low electrical conductivity, are found in the heart tissues. Consequently, the possibility of generating an arrhythmia becomes very high. The conduction velocity, v, affects Sh. In other words, the generation of arrhythmias is closely associated with the shim number.

The conduction velocity and diffusion coefficient in the shim number can be measured by using electrocardiographic or catheter insertion methods. The characteristic length L of a tissue and the characteristic length l of a cell can be obtained from computed tomography (CT), sonic CT, or electron microscopy images.

Preparatory Consideration Through Computer Simulation

Regarding this application, we can simplify the discussion by using two-dimensional heart surface tissues. While the cardiac muscles have three-dimensional characteristics and anisotropy in the electrical conductivity of tissues, two-dimensional analysis is used extensively as a model for analyzing heart diseases. In this embodiment, the analysis was conducted using two-dimensional tissue in Tusscher K. H., D. Noble, P. J. Noble, and A. V. Panfilov, A model for human ventricular tissue, Am J Physiol Heart Circ. Physiol, 2004, 286 (4), p. H1573-89. The discussion here focuses on analyzing whether tachycardia or fibrillation occurs depending on the shim number in heart tissue.

Figure 2:
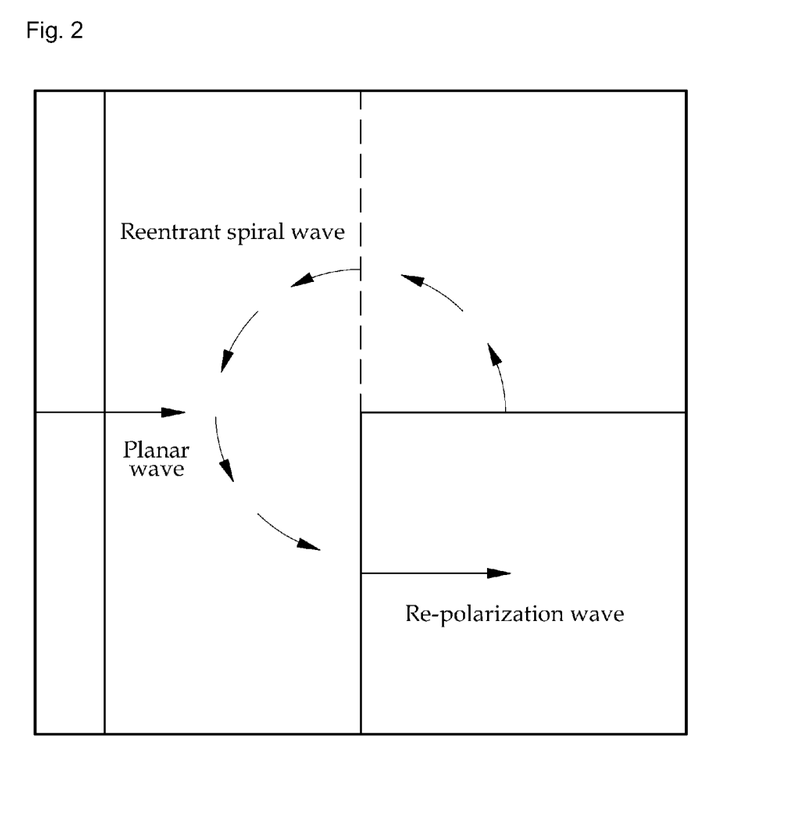
FIG. 2 explains the influence of an S2 wave on an S1 wave in a two-dimensional heart model.

As shown in FIG. 2, the imaginary heart is modeled as a rectangle. The S1 wave is a planar wave propagated from left to right. The external disturbing S2 wave is a reentrant spiral wave that affects the S1 wave, generating a re-polarization wave.

Figure 3:
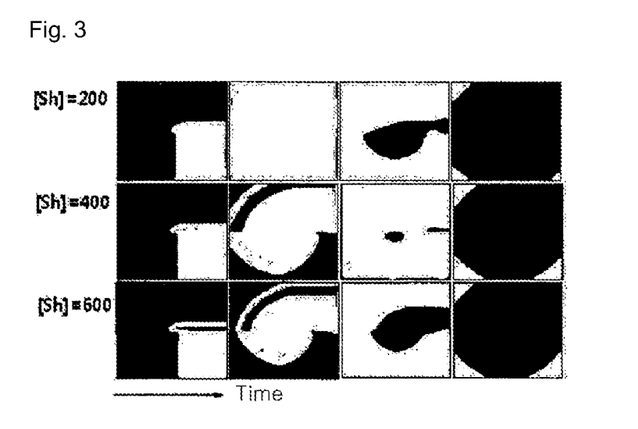
FIG. 3 shows the propagation of an action voltage with time for shim numbers [Sh] of 200, 400, and 600 in the two-dimensional heart model.
Figure 4:
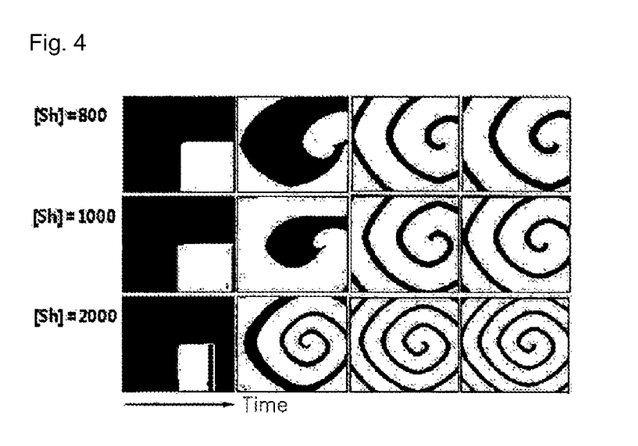
FIG. 4 shows the propagation of an action voltage with time for [Sh]=800, 1000, and 2000 in the two-dimensional heart model.

The propagation of an action voltage in the imaginary heart depending on the shim number is shown in FIGS. 3 to 6. Referring to FIG. 3, note that even if an external wave is applied to generate tachycardia-causing conditions in hearts with [Sh]=200, 400, and 600, the influence of the external wave disappears eventually. In FIG. 4, when an external wave is applied to produce tachycardia-causing conditions in hearts with [Sh]=800, 1000, and 2000, the influence of the external wave disappears, but tachycardia is generated.

Figure 5:
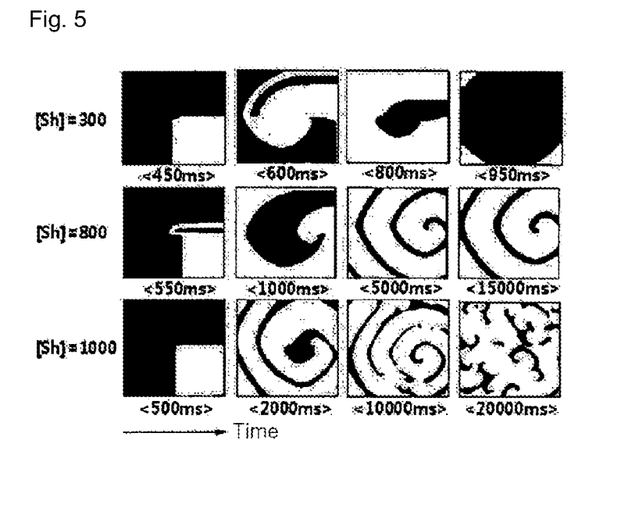
FIG. 5 shows the propagation of an action voltage with time for [Sh]=300, 800, and 1000 in the two-dimensional heart model with unstable cell tissues.

FIG. 5 shows that different results are obtained when an external wave is applied to hearts containing unstable cells with an altered ion current and with [Sh]=300, 800, and 1000. Specifically, the heart with [Sh]=300 returns to the normal state after 950 ms, the heart with [Sh]=800 fails to return to normal even after 1500 ms and tachycardia is generated, while for [Sh]=1000, tachycardia is induced with ease after 2000 ms and fibrillation develops after 20,000 ms. These results indicate that generation of an arrhythmia can be predicted by using the value of [Sh] specific to a patient. The simulations demonstrate that [Sh] is a decisive factor in generating and maintaining tachycardia and fibrillation.

Figure 6:
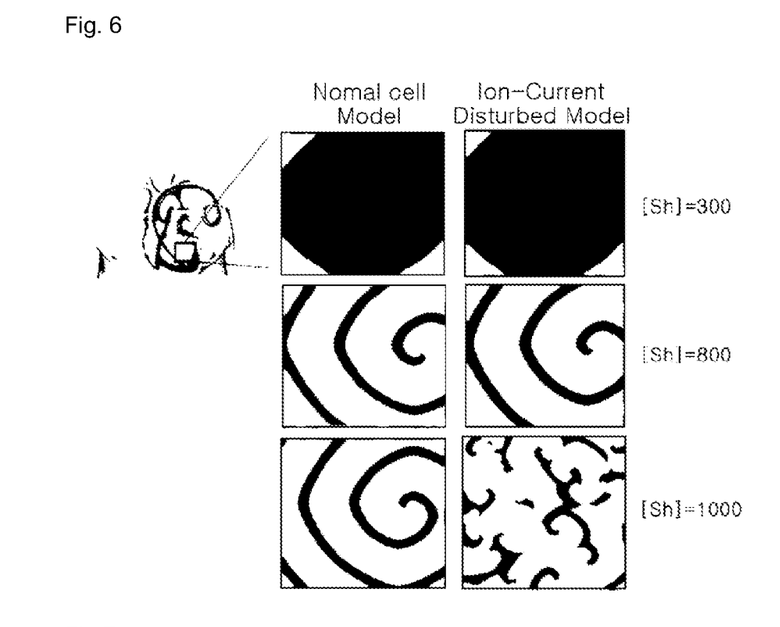
FIG. 6 shows models of normal and disturbed cells at a specified time after applying the conditions that cause tachycardia.

FIG. 6 shows images of normal and disturbed cell models at a specified time after applying the conditions that cause tachycardia. Even if [Sh] is identical, the probability of generating tachycardia and fibrillation depends on whether the heart model is a normal or disturbed cell model. Note that the probability of generating tachycardia and fibrillation increases with Sh. The colors in FIGS. 3-6 indicate the voltage distribution in the cell membrane: red indicates the excited state and blue the relaxation period.

As set forth above, the non-dimensional number [Sh] is a very important parameter in diagnosing arrhythmia. We will now describe a method and device used for diagnosing arrhythmia using Sh.

Figure 7:
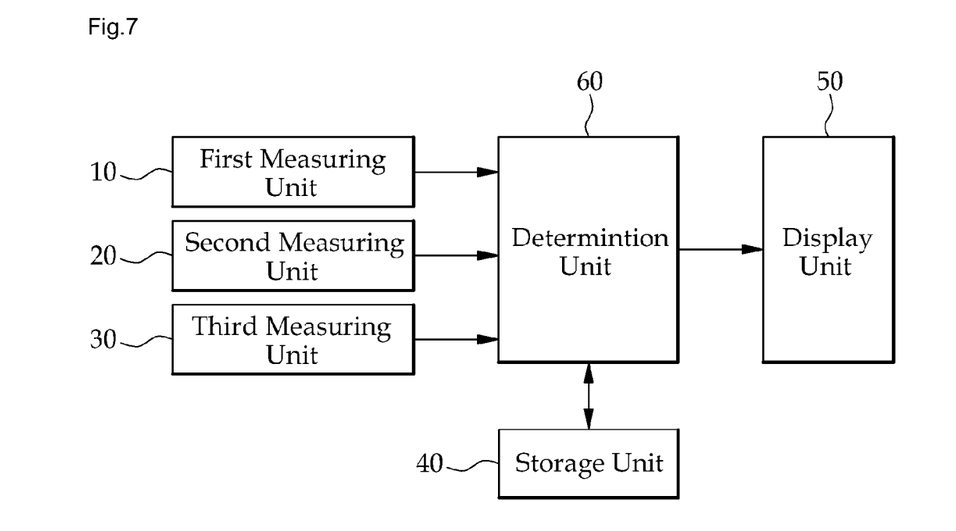
FIG. 7 is a schematic block diagram showing the arrhythmia-diagnosing device with one version of our invention.

FIG. 7 is a schematic diagram showing one version of our arrhythmia-diagnosing device. This device includes three measuring units (10, 20, and 30), and storage (40), display (50), and determination (60) units.

Unit 10 measures the heart characteristic length L, i.e., the length of the route through which the electrical wave passes in the heart. L is proportional to the size of the heart, and is called the characteristic length of the heart. Unit 10 is similar or identical to an echocardiograph and is configured to measure the heart characteristic length L. It may measure the heart characteristic length directly or measure the heart volume, if necessary. In the latter case, L is calculated as the cube root of the measured heart volume using formula 4.

$$L=l, L=\sqrt[3]{V}$$ [Formula 4]

where L is the heart characteristic length, l is the heart characteristic length measured by unit 10, and V is the heart volume measured by unit 10.

Unit 20 measures the frequency, f, of the cardiac electrical wave. It is similar to an electrocardiograph for outputting an ECG signal and is configured to measure the frequency of a cardiac electrical wave. The ECG signal contains R waves and the time interval between the R waves. The reciprocal of the time interval is the frequency of the cardiac electrical wave, as given by Formula 5, which unit 20 uses.

$$f = \frac{1}{RRinterval}$$ [Formula 5]

where $RR_{interval}$ is the time interval between R waves in the ECG signal.

Unit 30 measures the conduction velocity, CV, of the cardiac electrical wave. CV is determined using the ECG signal alone or the ECG signal and heart characteristic length. First, the CV of the cardiac electrical wave in the ventricle is calculated using the following formula.

$$CV = \frac{1}{QRS(\text{or } RS)}$$ [Formula 6]

where QRS is the QRS interval in the ECG signal, RS is the RS interval in the ECG signal, and CV is the conduction velocity of the cardiac electrical wave.

Next, the conduction velocity of the cardiac electrical wave in the atrium is calculated using the following formula.

$$CV = \frac{L}{P}$$ [Formula 7]

where L is the heart characteristic length and P is the width of the P wave in the ECG signal.

Unit 30 has the configurations of an echocardiograph and an electrocardiograph. It is configured to calculate and output the conduction velocity of the cardiac electrical wave using the ECG signal and heart characteristic length.

Storage unit 40 stores a reference value for the determination of arrhythmia. This value is compared with the magnitude of the non-dimensional number [Sh]. The reference value may have many different values. In our version, the reference value is set to a specific value ranging from 800-1200. This value can be changed by the user depending on a variety of factors, such the patient's age, sex, health, dietary habits, weight, and stature.

Display unit 50 shows the operating state of the arrhythmia-diagnosing device. Unit 50 includes liquid crystal displays (LCDs) and is capable of displaying [Sh] and the occurrence or absence of arrhythmia. There is a red LED that turns on when an arrhythmia is diagnosed and a green LED that turns on when no arrhythmia is diagnosed.

Unit 60 determines the occurrence or absence of an arrhythmia pursuant to the heart characteristic length and frequency and conduction velocity of the cardiac electrical wave input from measuring units 10 to 30, respectively. Unit 60 outputs a control signal to display unit 50 corresponding to the determination result.

First, determination unit 60 calculates the non-dimensional number [Sh] using Formula 8.

$$[Sh] = \frac{f \cdot L}{CV} \qquad \text{[Formula 8]}$$

where [Sh] is a non-dimensional number, f is the frequency of the cardiac electrical wave, L is the heart characteristic length, and CV is the conduction velocity of the cardiac electrical wave.

Subsequently, unit 60 compares [Sh] with the reference value stored in unit 40. If [Sh]≥the reference value, unit 60 determines that the heart suffers from arrhythmia. If [Sh]<the reference value, unit 60 determines that the heart does not suffer from arrhythmia. Determination unit 60 outputs a control signal corresponding to the result to display unit 50, which then displays the occurrence or absence of arrhythmia.

Figure 8:
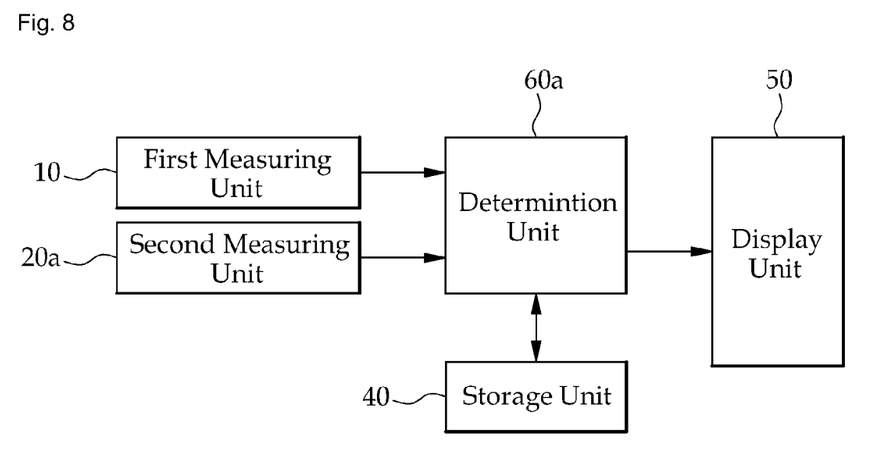
FIG. 8 is a schematic block diagram showing the arrhythmia-diagnosing device with another version of our invention.

FIG. 8 is a schematic block diagram showing another version of our arrhythmia-diagnosing device. This includes a second measuring unit 20*a* comprising an electrocardiograph. Accordingly, unit 20*a* outputs an ECG signal. As in the first version, unit 10 measures the heart characteristic length or heart volume. In the latter case, the heart characteristic length is calculated by unit 10 or determination unit 60*a*.

Determination unit 60*a* calculates the frequency of the cardiac electrical wave and its conduction velocity by using the heart characteristic length and the ECG signal. From this, unit 60*a* calculates [Sh]. By comparing the calculated value of [Sh] with the reference value, determination unit 60*a* determines the occurrence or absence of arrhythmia.

Figure 9:
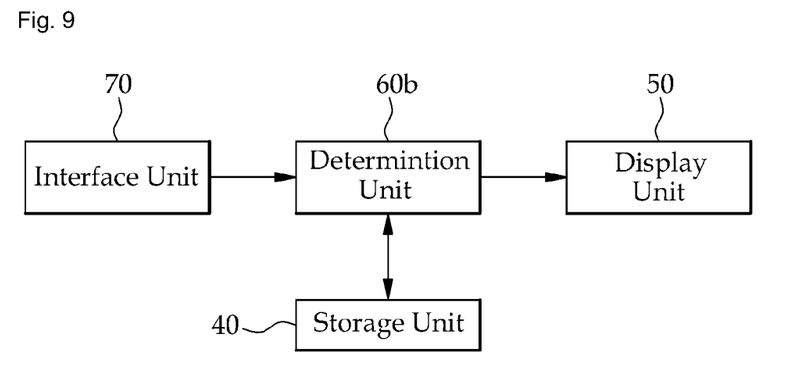
FIG. 9 is a schematic block diagram showing the arrhythmia-diagnosing device with a third version of our invention.

FIG. 9 is a schematic diagram showing a further embodiment of our arrhythmia-diagnosing device. This one includes interface unit 70, storage unit 40, display unit 50, and determination unit 60*b*.

Interface unit 70 enables wired or wireless communication with an echocardiograph or electrocardiograph. The heart characteristic length measured by the echocardiograph and the ECG signal, including the RR, QRS, and RS intervals and P wave width, output from the ECG are input to unit 60*b* via this interface unit. Unit 60*b* calculates the non-dimensional number [Sh] using the values input via interface unit 70. By comparing [Sh] with the reference value, unit 60*a* determines the occurrence or absence of arrhythmia and outputs a signal so that the result is displayed on unit 50. If necessary, the arrhythmia-diagnosing device can be configured such that the heart characteristic length and frequency and conduction velocity of the cardiac electrical wave are input via interface unit 70.

Several versions of the invention have been described above, but our invention is not limited to these. Changes and modifications may be made without departing from the scope of the invention defined in the claims.

What is claimed is:

1. A noninvasive arrhythmia-diagnosing method, comprising the steps of:
   (a) measuring a heart characteristic length;
   (b) measuring a frequency of the cardiac electrical wave;
   (c) measuring a conduction velocity of a cardiac electrical wave via an echocardiograph or an electrocardiograph; and
   (d) determining an occurrence or absence of arrhythmia using the heart characteristic length, the frequency, and the conduction velocity measured in the steps (a) to (c).

2. The noninvasive arrhythmia-diagnosing method of claim 1, wherein in the step (d), a non-dimensional number is obtained by processing the heart characteristic length and frequency and conduction velocity of the cardiac electrical wave measured in the steps (a) to (c) and is used to determine the occurrence or absence of arrhythmia.

3. The noninvasive arrhythmia-diagnosing method of claim 2, wherein the non-dimensional number is calculated as:

$$[Sh] = \frac{f \cdot L}{CV}, \qquad \text{[Formula 8]}$$

where [Sh] is the non-dimensional number, f is the frequency of the cardiac electrical wave, L is the heart characteristic length, and CV is the conduction velocity of the cardiac electrical wave.

4. The noninvasive arrhythmia-diagnosing method of claim 3, wherein it is determined in the step (d) that a heart suffers from arrhythmia if [Sh] ≥ a predetermined reference value.

5. The noninvasive arrhythmia-diagnosing method of claim 2, wherein the frequency of the cardiac electrical wave is measured using an ECG signal generated by an electrocardiograph and the conduction velocity of the cardiac electrical wave is measured using the ECG signal generated by the electrocardiograph or using the ECG signal and the heart characteristic length.

6. The noninvasive method of claim 5, wherein the heart characteristic length is calculated using $$L=1, L=\sqrt[3]{V}, \qquad \text{[Formula 4]}$$

the frequency of the cardiac electrical wave is calculated using $$f = \frac{1}{RRinterval}, \qquad \text{[Formula 5]}$$

and the conduction velocity of the cardiac electrical wave is calculated using $$CV = \frac{1}{QRS(\text{or } RS)} \qquad \text{[Formula 6]}$$

or $$CV = \frac{L}{P}, \qquad \text{[Formula 7]}$$

in formulas 4 through 7, l is the heart characteristic length measured by an echocardiograph, V is the heart volume measured by the echocardiograph, the $RR_{interval}$ is the time interval between R waves contained in the ECG signal, QRS is the QRS interval contained in the ECG signal, RS is the RS interval contained in the ECG signal, and P is the width of the P wave contained in the electrocardiogram signal, and Formula 6 is applied to the ventricle and Formula 7 to the atrium.

7. The noninvasive arrhythmia-diagnosing method of claim 3, wherein the heart characteristic length is calculated using $$L = l, L = \sqrt[3]{V} \quad \text{[Formula 4]}$$

the frequency of the cardiac electrical wave is calculated using $$f = \frac{1}{RRinterval}, \quad \text{[Formula 5]}$$

and the conduction velocity of the cardiac electrical wave is calculated using $$CV = \frac{1}{QRS(\text{or } RS)} \quad \text{[Formula 6]}$$

or $$CV = \frac{L}{P}, \quad \text{[Formula 7]}$$

in formulas 4 through 7, l is the heart characteristic length measured by an echocardiograph, V is the heart volume measured by the echocardiograph, the $RR_{interval}$ is a time interval between R waves contained in the ECG signal, QRS is a QRS interval contained in the ECG signal, RS is an RS interval contained in the ECG signal, and P is a width of a P wave contained in the electrocardiogram signal, Formula 6 is applied to a ventricle and Formula 7 to a atrium, and It is determined that the heart suffers from an arrhythmia if [Sh] >800 to 1200.

8. The noninvasive arrhythmia-diagnosing method of claim 1, wherein measuring a conduction velocity of a cardiac electrical wave is via an echocardiograph.

9. The noninvasive arrhythmia-diagnosing method of claim 1, wherein measuring a conduction velocity of a cardiac electrical wave is via an electrocardiograph.

* * * * *